United States Patent
Wang et al.

(10) Patent No.: US 11,479,592 B2
(45) Date of Patent: Oct. 25, 2022

(54) ERYTHROPOIETIN-DERIVED PEPTIDE, PREPARATION METHOD AND USE THEREOF

(71) Applicant: Zhongshan Hospital, Fudan University, Shanghai (CN)

(72) Inventors: Xin Wang, Shanghai (CN); Jing Ding, Shanghai (CN); Tingting Wu, Shanghai (CN)

(73) Assignee: ZHONGSHAN HOSPITAL, FUDAN UNIVERSITY, Shanghai (CN)

( * ) Notice: Subject to any disclaimer, the term of this patent is extended or adjusted under 35 U.S.C. 154(b) by 945 days.

(21) Appl. No.: 16/320,493

(22) PCT Filed: Mar. 7, 2018

(86) PCT No.: PCT/CN2018/078253
§ 371 (c)(1),
(2) Date: Jan. 25, 2019

(87) PCT Pub. No.: WO2019/085366
PCT Pub. Date: May 9, 2019

(65) Prior Publication Data
US 2021/0171595 A1 Jun. 10, 2021

(30) Foreign Application Priority Data
Nov. 1, 2017 (CN) .......................... 201711058179.6

(51) Int. Cl.
C07K 14/505 (2006.01)
A61P 25/00 (2006.01)
C12N 15/63 (2006.01)
A61K 38/00 (2006.01)

(52) U.S. Cl.
CPC ............ *C07K 14/505* (2013.01); *A61K 38/00* (2013.01); *A61P 25/00* (2018.01); *C12N 15/63* (2013.01)

(58) Field of Classification Search
None
See application file for complete search history.

(56) References Cited

U.S. PATENT DOCUMENTS

| 2014/0005109 A1* | 1/2014 | Rex .......................... | C12N 15/86 514/7.7 |
| 2016/0271206 A9* | 9/2016 | Lu ....................... | A61K 38/1816 |

FOREIGN PATENT DOCUMENTS

| CN | 102205114 A | 10/2011 |
| CN | 103450348 A | 12/2013 |
| CN | 105148257 A | 12/2015 |
| CN | 106928338 A | 7/2017 |
| EP | 2762149 A2 | 8/2014 |
| WO | 2007052154 A2 | 5/2007 |
| WO | 2008065372 A2 | 6/2008 |
| WO | 2009094172 A2 | 7/2009 |
| WO | 2012097256 A1 | 7/2012 |

OTHER PUBLICATIONS

M. Brines, et al., Erythropoietin-mediated tissue protection: reducing collateral damage from the primary injury response, Journal of Internal Medicine, Nov. 1, 2008, pp. 405-432, vol. 264, No. 5.
Francis Dumont, et al., Non-erythropoietic tissue-protective peptides derived from erythropoietin, Expert Opinion on Therapeutic Patents, Mar. 2, 2010, pp. 715-723, vol. 20, No. 5.
Stanislava Pankratova, et al., Neuroprotective propedies of a novel non-haematopoietic agonist of the eryhropoietin receptor, Brain, Aug. 1, 2010, pp. 2281-2294, vol. 133, No. 8.
Michael Brines et al, Nonerytropoietic, tissue-protective peptides derived from the tertiary structure of erytropoietin PNAS Aug. 5, 2008, issue 31, vol. 105, pic 1, abstract, p. 10925-10929.
Gu Bing et al., Review on the neuroprotective effect of erythropoietin derivatives, Chinese Pharmacological Bulletin Apr. 2012; 28( 4): 458-461.
Liu Y et al, Erythropoietin-Derived Nonerytlrropoietic Peptide Ameliorates Experimental Autoimmune Neuritis by Inflammation Suppression and Tissue Protection PLOS ONE 06.March.
Yu Gan, et al., Mutant Erythropoietin Without Erythropoietic Activity Is Neuroprotective Against Ischemic Brain Injury, Stroke,Sep. 13, 2012, pp. 3071-3077, vol. 43, No. 11.
Stanislava Pankratova, et al., Neuroprotective properties of a novel, non-haematopoietic agonist of the erythropoietin receptor. Brain, 2010, pp. 2281-2294, vol. 133, No. Pt 8.
Michael Brines, et al., Erythropoietin mediates tissue protection through an erythropoietin and common β-subunit heteroreceptor, PNAS, Oct. 12, 2004, pp. 14907-14912, vol. 101, No. 41.
Michael Brines, et al., Nonerythropoietic, tissue-protective peptides derived from the tertiary structure of erythropoietin, PNAS, Aug. 5, 2008, pp. 10925-10930, vol. 105, No. 31.

(Continued)

*Primary Examiner* — Adam Weidner
(74) *Attorney, Agent, or Firm* — Bayramoglu Law Offices LLC (57) ABSTRACT

An erythropoiet-derived peptide having an amino acid sequence as shown in SEQ ID NO: 1. A, method for preparing the above-described erythropoietin-derived peptide. Also provided is the rrse of the above-described erythropoietin-derived peptide fo the preparation of medicament for reatin$ nerve cell damage. Also provided is the use of the above-described erythropoietin-derived peptide for the preparation of a medicament for treating hypoxic brain damage. Also provided is the use of the above-described erythropoietin-derived peptide for the preparation of a medicament for treating epilepsy. The novel EPO-derived peptide of the present invention has a small molecular weight and can penetrate the blood-brain barrier. Moreover, it is a small-molecule polypeptide derived from a functional protein in the human body, having an extremely small side effect to the human body compared with other developed and synthesized thugs, thereby it has a good clinical application prospect.

19 Claims, 6 Drawing Sheets

Specification includes a Sequence Listing.

(56) References Cited

OTHER PUBLICATIONS

Yuqi Liu, Erythropoietin-Derived Nonerythropoietic Peptide Ameliorates Experimental Autoimmune Neuritis by Inflammation Suppression and Tissue Protection, PLOS ONE, Mar. 2014, pp. 1-11, vol. 9, Issue 3.

* cited by examiner

ERYTHROPOIETIN-DERIVED PEPTIDE, PREPARATION METHOD AND USE THEREOF

CROSS REFERENCE TO RELATED APPLICATIONS

This application is the national phase entry of International Application No. PCT/CN2018/078253, filed on Mar. 7, 2018, which is based upon and claims priority to Chinese Patent Application No. 201711058179.6, filed on Nov. 1, 2017, the entire contents of which are incorporated herein by reference.

TECHNICAL FIELD

The present invention belongs to the field of genome biology, and relates to an erythropoietin, specifically to an erythropoietin-derived peptide, preparation method and use thereof.

BACKGROUND

With the prolongation of human lifespan, nervous system diseases are increasingly becoming a heavy burden for patients, families and society. In 2016, The Lancet published a new global cause-of-death analysis report from the Global Burden of Disease (GBD), which revealed that the ranking of the cause of death from cerebrovascular disease rose again in 2015, jumping to the second leading cause of human death. In China, cerebrovascular disease is the first leading cause of death and disability in China's population. The prevalence rate thereof is increasing year by year and patients thereof tend to be younger. Moreover, the incidence of other nervous system diseases such as Alzheimer's disease, other types of dementia, epilepsy, and Parkinson's disease are also increasing year by year, and the death rate has increased by more than 20% from 1990 to 2015. In addition to affecting health, nervous system diseases represented by cerebrovascular diseases have caused a certain economic burden on the state and the society. The World Health Organization (WHO) calculates and finds that a 10% of the reduction in mortality from stroke and myocardial infarction is expected to reduce the annual expenditure of about $25 billion for interventions. In a sense, nervous system diseases are not only medical problems, but also social problems.

Due to the complicated pathogenesis and numerous symptoms, there are still many kinds of nervous system diseases that lack effective drug treatment. Taking hypoxic encephalopathy as an example, a hyperbaric oxygen chamber can improve oxygen supply for brain tissue, but it is contraindicated in poorly controlled hypertensive patients and critically ill patients, and may have adverse effects caused by secondary cerebral vasoconstriction, thus limiting clinical application. Taking ischemic stroke disease as another example, a series of pathophysiological such as energy metabolism disorder, excitatory amino acid toxicity, etc. are changed after cerebral ischemia. Thrombolysis is the only effective treatment currently, but the time window of thrombolytic therapy is so short that only a few patients benefit. Another way is neuroprotective treatment, which blocks the death of nerve cells and saves nerve cells in the ischemic penumbra. Currently, the main neuroprotective agents that may have protective effects includes: glutamate antagonists, anti-inflammatory factors, calcium channel blockers, sodium channel blockers, potassium channel activators, free radical scavengers, GABA receptor antagonists, serotonin antagonists, NMDA receptor antagonists, phenobarbital drugs for inducing anesthesia at low temperature, etc. At present, more than 1,000 neuroprotective agents are effective in animal experiments, and more than 100 drugs have been clinically tested, but have achieved little clinical effect. Therefore, it is of great significance to develop new effective neuroprotective agents.

Erythropoietin (EPO) is a 34 kDa glycoprotein hormone composed of 165 amino acids and mainly produced by the kidney, which is the earliest clinically applied cytokine. In the past, the erythropoietin was widely used in the treatment of anemia in the clinic. Recent studies suggest that EPO and EPO receptors (EPOR) are also widely distributed in various non-hematopoietic tissues including nerves, heart, kidneys, etc. It is a multifunctional molecule with extensive tissue protective activity. In particular, researches of recent 20 years have found that EPO can play a neuroprotective and neurotrophic role in experiments both in vivo and in vitro.

In the nervous system, EPO/EPOR is expressed in neurons, astrocytes, vascular endothelial cells, etc. EPO/EPOR is in a low expression state in normal adult brain tissue, but its expression is significantly increased when the brain tissue is damaged or has suffered stress such as ischemia, hypoxia, etc. However, the activated EPO/EPOR system is not sufficient to protect the damaged nerve cells, and if a large amount of exogenously supplemented recombinant erythropoietin (rhEPO) enters the nervous system through the blood-brain barrier by receptor-mediated endocytosis or pinocytosis on the cell membrane. EPO combines with overexpressed EPOR to induce Jak2 phosphorylation, thus activating signal transductants and pathways including transcriptional activator STAT5 pathway, phosphatidylinositol 3 kinase (P13K)/AKT pathway, nuclear factor NF-κB pathway, etc. Neuronal apoptosis and neuronal damage are reduced through a combination of various mechanisms such as anti-inflammatory, anti-oxidative stress, anti-apoptosis, inhibition of excitotoxicity, promotion of nerve regeneration, protection of blood-brain barrier, etc., thus exerting neuroprotective effects. Moreover, the neuroprotective effects of EPO have been confirmed in a variety of animal disease models, including: cerebral ischemia, cerebral ischemia and hypoxia damage, cerebral ischemia-reperfusion damage, spinal cord damage, experimental autoimmune encephalomyelitis (EAE), subarachnoid hemorrhage, epilepsy, Parkinson's disease, multiple system atrophy, sciatic nerve compression, retinal ganglion cell damage, etc.

After EPO has been confirmed to have neuroprotective effects both in vitro and in vivo, in recent decades, a series of clinical trials in patients from cerebral ischemia, nerve damage to inflammation and neurodegeneration, have further investigated whether EPO can exert neuroprotective effects and regenerative functions in humans. Fortunately, most of these studies have confirmed that EPO treatment is effective. However, as EPO has the effect of promoting erythropoiesis, high-dose or long-term use of EPO can directly lead to a series of serious medical problems such as polycythemia, hypertension, thrombosis, etc. Therefore, the development of the preparations of EPO derivatives, allosteric, etc. that have no hematopoietic function but have neuroprotective effects has become a research hotspot for neuroscientists at present.

In recent years, researchers have developed some EPO derivatives with neuroprotective effects but without erythropoiesis effects. One kind of the EPO derivative is represented by carbamylated EPO (CEPO) including the modified erythropoietin protein derivatives such as asialoEPO, Neuro-EPO, etc. With the in-depth research of EPO and CEPO, it is found that CEPO does not combine with EPOR but can also preserve the neuroprotective and other tissue protection effects of EPO. Therefore, it is further proposed that the tissue protective effect of EPO, including neuroprotection, is mediated by a heteropolymer composed of EPOR and CD131, i.e., βcR (β complex), which is different from the erythropoiesis effect of EPO that is mediated by a dimer composed of two EPOR molecules. Another kind of the EPO derivative is a low molecular weight peptide that mimics the EPO spatial structure, including HBP, HBSP (ARA290), pHBSP, Epopeptide AB, MKX-2, JM4, Epotris, etc. This kind of polypeptide derivative has the advantages of low molecular weight and easily penetrates the blood-brain barrier, which has a promising clinical application. However, further research and experiments are needed to be clinically performed in order to verify the effects on the human body.

SUMMARY

In view of the above technical problems in the prior art, the present invention provides an erythropoietin-derived peptide, preparation method and use thereof. The erythropoietin-derived peptide has no erythropoiesis effect, but has neuroprotective effects, which can avoid a series of serious medical problems such as polycythemia, hypertension, thrombosis, etc. caused by the erythropoiesis effect.

511-6), and part of the amino acid are deleted (For example, one or more positions selected from the group consisting of glutamine at position 86, tryptophan at position 88, glutamate at position 89, proline at position 90, and lysine at position 97 in the amino acid sequence of the EPO molecule are deleted, and preferably all of the above positions are deleted.). When the original arginine at position 103 is replaced with alanine, the erythropoietin-derived peptide loses erythropoiesis effects, but has neuroprotective effects.

One aspect of the present invention provides an erythropoietin-derived peptide having no erythropoiesis effect but having neuroprotective effects, which includes the following (a) or (b):

(a) a polypeptide with an amino acid sequence as shown in SEQ ID NO: 1;

(b) a polypeptide derived from the polypeptide in (a) subjected to substitution, deletion or addition of one or several amino acids.

Specifically, SEQ ID NO: 1 is:

SEAVLRGQAL LVNSSP LQLHVDAVSGLASLTTLLRAL.

In a preferred implementation mode of the present invention, the amino acid sequence of the erythropoietin-derived peptide is the sequence as shown in SEQ ID NO: 1.

Further, the erythropoietin-derived peptide having the above-described amino acid sequence as shown in SEQ ID NO: 1 has the following structural formula:

The present invention first refers to the disclosed amino acid sequence of human EPO (Proteomic databases, P01588), one segment of the amino acid sequence containing the EPO and EPOR binding sites and the EPO protein helix structure is selected according to the research results published in Nature in 1998 (Nature, 1998. 395(6701): p.

Another aspect of the present invention provides a medicament including the erythropoietin-derived peptide, or a composition including the erythropoietin-derived peptide.

Further, the present invention provides a pharmaceutical composition including the erythropoietin-derived peptide and an excipient or carrier. When administered, the pharmaceutical compositions of the present invention are administered in a pharmaceutically acceptable preparation. The preparation routinely includes pharmaceutically acceptable concentrations of salts, buffers, preservatives, compatible carriers, and optionally other therapeutic agents.

Another aspect of the present invention provides a nucleic acid molecule including a nucleotide sequence encoding any of the above-described erythropoietin-derived peptides.

Further, the present invention also provides an expression vector of the above-described nucleic acid molecule.

Further, the present invention also provides a host cell or virus of the above-described expression vector.

Further, the present invention also provides a kit including any one of the following:

a) the erythropoietin-derived peptide in the present invention;
b) the composition in the present invention;
c) the nucleic acid molecule in the present invention;
d) the expression vector in the present invention;
e) the host cell in the present invention;
f) the virus in the invention.

The present invention also provides a preparation method of the above-described erythropoietin-derived peptide, including the following steps:

1) adopting a solid phase synthesis method, immersing a starting resin attached with leucine in DMF (N,N-dimethylformamide) for 20 to 50 min, and then immersing in a decapping solution to remove FMOC (fluorenylmethoxycarbonyl) for 20 to 50 min, and washing with dimethylformamide;

2) adding a next amino acid, condensing agent and base, reacting for 20 to 50 min, and then washing with dimethylformamide;

3) removing FMOC with the decapping solution, and then washing with dimethylformamide after 30 min:

4) repeating steps 2) and 3) to sequentially link amino acids.

Further, the linkage order of the amino acids in the preparation method of the present invention is as follows: leucine→alanine→arginine→leucine→leucine→threonine→threonine→leucine→serine→alanine→leucine→glycine→serine→valine→alanine→aspartate→valine→histidine→leucine→glutamine→leucine→proline→seine→serine→asparagine→valine→leucine→leucine→alanine→glutamine→glycine→arginine→leucine→valine→alanine→glutamate→serine.

Preferably, the condensing agent in step 2) is TBTU, i.e., O-benzotriazole-N,N,N',N'-tetramethyluronium tetrafluoroborate.

Preferably, the base in step 2) is morpholine.

Preferably, the decapping solution in step 3) is a mixture of hexahydropyridine and N, N-dimethylformamide, wherein the volume ratio of the hexahydropyridine to the N, N-dimethylformamide is preferably 1:3 to 5, and most preferably 1:4.

The present invention also provides a use of the above-described erythropoietin-derived peptide for treating nerve cell damage.

The present invention also provides a use of the above-described erythropoietin-derived peptide for treating hypoxic brain damage.

The present invention also provides a use of the above-described erythropoietin-derived peptide for treating epilepsy.

The present invention also provides a medicament for treating nerve cell damage including the erythropoietin-derived peptide of the present invention.

The present invention also provides a medicament for treating hypoxic brain damage including the erythropoietin-derived peptide of the present invention.

The present invention also provides a medicament for treating epilepsy including the erythropoietin-derived peptide of the present invention.

The present invention successfully prepares and synthesizes a novel EPO-derived peptide, and the purity of the novel EPO-derived peptide can reaches 95% by using the preparation method of the present invention.

To further investigate the function of the novel EPO-derived peptide, the inventors designed an animal model of epilepsy. After the EPO-derived peptide was administered in the animal model, the seizure latency was prolonged, indicating that it may have the effect of alleviating nerve cell damage. Further experiments confirmed that, after the novel EPO-derived peptide was administered in animals with nerve damage, the novel EPO-derived peptide can protect neurons during acute injury, penetrate the blood-brain barrier to exert neuroprotective effects and prolong the seizure latency, and can reduce the loss of neurons in the hippocampus, thus indicating that the novel EPO-derived peptide has a medicinal effect for treating nerve damage.

The novel EPO-derived peptide of the present invention has shown to have an anti-neuronal apoptosis effect in vitro. After the primary cultured neurons were administered to have oxygen-glucose deprivation-induced damage and NMDA-induced damage, the neuronal damage in the novel EPO-derived peptide intervention group was alleviated, and the cell survival rate was higher than that of the control group. In vivo, it was verified that novel EPO-derived peptide can reduce cerebral infarction volume, improve cerebral ischemia, and reduce the severity measured by neurobehavioral scores, thus suggesting that the novel EPO-derived peptide can alleviate nerve damage, have neuroprotective effects, and reduce apoptosis. Long-term administration to mice has no side effect of significantly promoting erythropoiesis. Thus, the novel EPO-derived peptide has a neuroprotective effect on acute hypoxic damage and is better than EPO.

Compared to the prior art, the technical progress of the present invention is remarkable. The present invention provides a novel EPO-derived peptide having neuroprotective effect without erythropoietic activity. The new drug has a low molecular weight, can penetrate the blood-brain barrier. Moreover, the new drug is a low-molecule weight polypeptide derived from a functional protein of the human body, having an extremely small side effect to the human body compared with other developed and synthesized drugs, and having a good clinical application prospect. If the present invention is applicable to clinical practice, it will become a novel neuroprotective drug for preventing and treating central nervous system diseases, and can provide a new therapeutic direction for patients with nerve damage.

DETAILED DESCRIPTION OF THE EMBODIMENTS

Embodiment 1: Preparation of the EPO-Derived Peptide of the Present Invention Steps for synthesizing the EPO-derived peptide of the present invention: leucine is used as the starting resin, the starting resin is immersed in dimethylformamide for 30 min, and then decapping solution is used to remove fluorenylmethoxycarbony, after 30 min, dimethylformamide is used to wash; the next amino acid (alanine), condensing agent and base are added to react for 30 min, and then dimethylformamide is used to wash and detect: after a successful detection, fluorenylmethoxycarbony is removed with the decapping solution, and then dimethylformamide is used to wash after 30 min; then, the next amino acid (arginine) is linked according to the designed sequence until the last amino acid was linked; on the basis of ensuring the correctness of the linear peptides, the EPO-derived peptide is cut and purified to reach a purity of over 95% finally.

Figure 1:
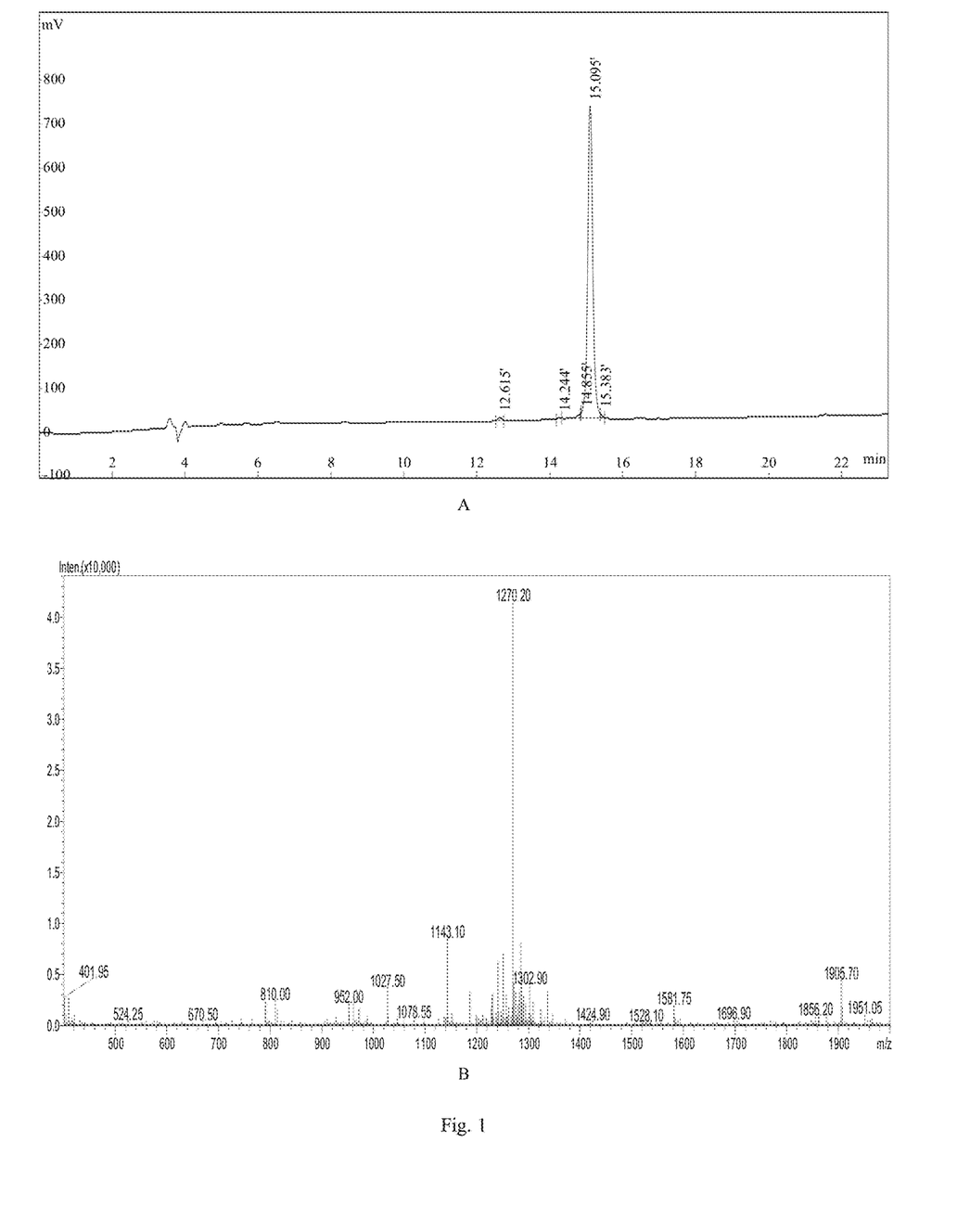
FIG. 1A is High Performance Liquid Chromatography (HPLC) report and FIG. 1B is Mass Spectrometry report.

Method for identifying the purity of the novel EPO-derived peptide: see FIG. 1A and FIG. 1B.

The crude peptides are dissolved in an acetonitrile aqueous solution, a ratio of ACN (acetonitrile) to $H_2O$ thereof is 1:2 by volume. HPLC purification is performed. HPLC conditions: mobile phase A phase: 0.1% TFA (trifluoroacetic acid)/100% ACN (acetonitrile); mobile phase B phase: 0.1% TFA (trifluoroacetic acid)/100% water; chromatographic column: Kromasil C18, 4.6×250 mm, 5 µm;

| Gradient | A | B |
|---|---|---|
| 0.0 min | 38% | 62% |
| 25.0 min | 63% | 37% |
| 25.1 min | 100% | 0% |
| 30.0 min | Stop | |
| Flow rate | 1.0 ml/min | |
| Column temperature | 25° C. | |

After setting the equilibration of the instrument, the instrument was started to run for about 10 min. The crude peptides were injected into the instrument, the baseline was collected, and the instrument was stopped. Finally, a sample with a purity of 95.25% was obtained.

Embodiment 2: Hematopoietic Experiment of the EPO-derived Peptide of the Present Invention 18-22 g of male C57/BL6 mice (purchased from Shanghai SIPPR-BK Laboratory Animal Co., Ltd., 50 mice in total and 10 mice for each group) were used. The five groups were injected intraperitoneally with EPO (50 µg/kg), EPO-derived peptide of the present invention (50 µg/kg), EPO-derived peptide of the present invention (250 µg/kg), physiological saline (0.1 m/mouse), and solvent (ACN+Milliq, 0.1 m/mouse) once a day, respectively. On the 3th, 7th, and 13th days, the blood samples were collected from the tail vein and measured by a ProCyte Dx automatic blood cell analyzer to obtain the numbers of red blood cells thereof.

The experimental results are shown in Table 1:

TABLE 1

| RBC generation comparison table (3th, 7th, and 13th days) Unit: M/µL | | | | | |
|---|---|---|---|---|---|
| | Saline | ACN + Milliq | T3 50 ug/kg | T3 250 ug/kg | Epo 50 ug/kg |
| 3th day | 7.03 ± 0.59 | 8.10 ± 0.44 | 9.29 ± 0.13 | 8.16 ± 0.28 | 9.14 ± 0.56 |
| 7th day | 7.36 ± 0.47 | 8.63 ± 0.52 | 8.75 ± 0.36 | 9.56 ± 0.54 | 12.79 ± 0.24 |
| 13th day | 6.28 ± 0.17 | 5.81 ± 0.14 | 6.77 ± 0.18 | 6.52 ± 0.12 | 11.15 ± 0.23 |

Figure 2:
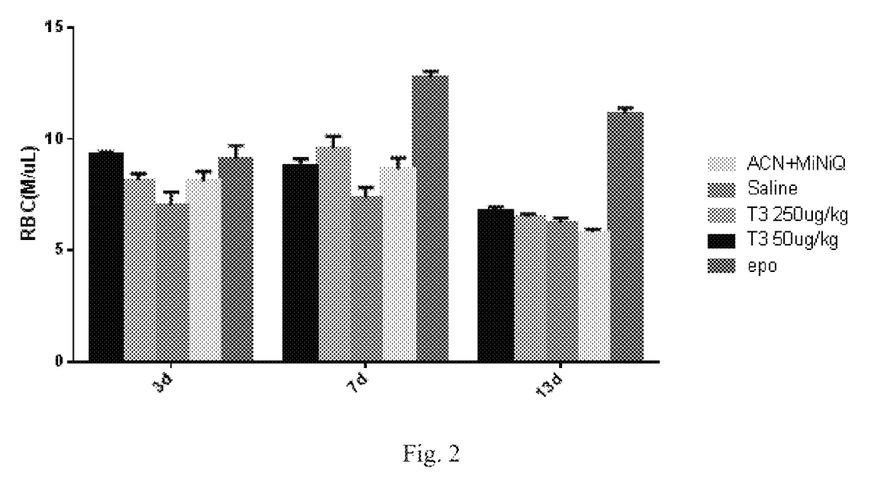
FIG. 2 is a histogram of the comparison of the erythrocyte counts (3th day, 7th day, 13th day), wherein the abscissa represents detection day, and the ordinate represents erythrocyte counts (M/μL).

The above data presented in a histogram is as shown in FIG. 2. It can be seen that, as the number of administrations increases, the red blood cell counts of the EPO group is significantly higher than that of other groups. However, the red blood cell counts of the EPO-derived peptide groups (T3) of the present invention have no significant increase compared with that of the physiological saline group (Saline) and the solvent group (ACN+Milliq). Moreover, the difference between the red blood cell counts of the high-dose EPO-derived peptide group and that of the low-dose group was also not statistically significant.

Figure 3:
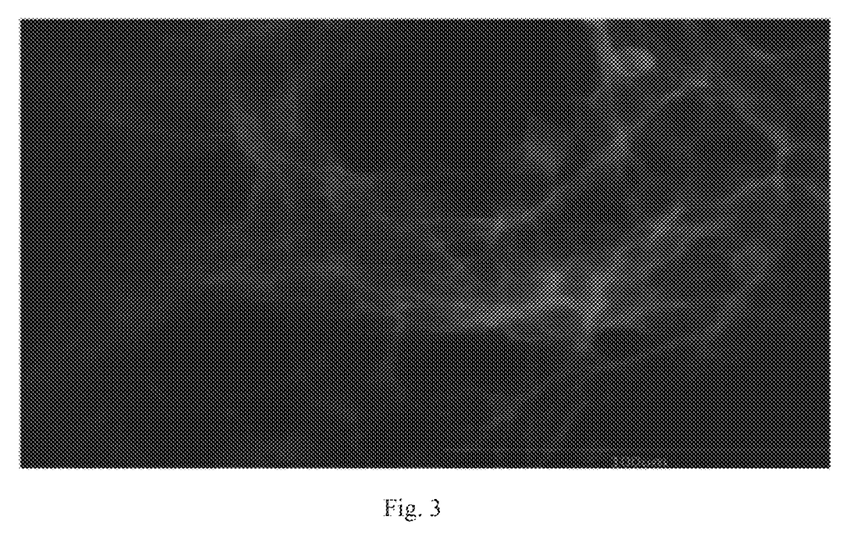
FIG. 3 is a fluorescent double staining image of MAP-2 and DAPI in cortical neurons.

Embodiment 3: Neuron Protection Experiment of the EPO-Derived Peptide of the Present Invention According to the methods from literatures, the fetal rat cortical neurons were cultured in the serum-free culture medium of Neurobasal® Medium (purchased from the market). After incubation in a 5% $CO_2$ incubator for 7-14 days, the neurons were specifically labeled: microtubule-associated protein-2 (MAP-2) was stained and identified, and the nuclei were labeled with the fluorescent dye of 4, 6-diamidino-2-phenylindole (DAPI). The results observed under a fluorescence microscope are shown in FIG. 3.

The specific operation process is as follows:

Primary Culture of Fetal Rat Cortical Neurons

1. Anesthetizing an SD pregnant rat on gestation day 18 (Shanghai SIPPR-BK Laboratory Animal Co., Ltd.) with 10% chloral hydrate;

2. Disinfecting the abdominal skin with 75% alcohol, opening the abdominal cavity, separating the uterus, and taking out the fetal rat;

3. Separating the tissue: cutting the head of the fetal rat, and immediately putting it into the pre-cooled PBS buffer; operating on ice, carefully separating the brain tissue, carefully separating the cortex, carefully peeling off the meninges and blood vessels, and washing with the PBS solution twice;

4. Shredding: shredding the cortex with ophthalmic scissors to obtain cortex fragment of about 1 $mm^3$;

5. Digestion: moving the shredded tissue blocks into a clean 50 ml centrifuge tube, adding 5 ml of 0.125% trypsin-EDTA pre-heated to 37° C., and digesting in a water bath at 37° C. for about 5-10 min;

6. Stopping digestion: stopping the digestion by adding 5 ml of FBS-DMEM culture medium pre-heated to 37° C.; aspirating the flocculent cell mass into a clean 15 ml centrifuge tube, and adding 10% FBS-DMEM culture medium to wash away the residual digestive solution;

7. Repeated pipetting through a dropper to disperse into single cells, and filtering the cells through a 200 mesh filter to obtain a single cell suspension;

8. Centrifuging at 2000 rpm and at 4° C. for 5 min, discarding the supernatant, adding the seeding culture medium containing 10% fetal bovine serum to resuspend the cells;

9. Counting under a microscope, seeding at a density of $1 \times 10^6/cm^2$ on glass slides or culture plates polylysine-coated overnight, and incubating in a 5% $CO_2$ incubator with 95% humidity at 37° C.;

10. After culturing for 8-12 h, replacing all culture medium with NeurobasalA+B27+ glutamine serum-free culture medium to maintain the culture, and changing the culture medium every three days.

11. Performing neuron identification after 7-14 days.

Neuron Identification by MAP-2/DAPI

1. Selecting the neurons cultured on glass slides for 7-14 days and washing with pre-heated PBS for 5 min;

2. Adding 4% paraformaldehyde to fix for 30 min at room temperature;

3. Washing 3 times with PBS, 5 min each time;

4. Adding 0.2% TritonX-100 PBS to permeabilize the membrane for 20 min at room temperature;

5. Washing 3 times with PBS, 5 min each time;

6. Blocking: adding blocking solution (5% goat serum), and blocking at room temperature for 30-60 min;

7. After aspirating the liquid, adding the primary antibody (rabbit anti-MAP-2 polyclonal antibody, Abcam) at a dilution of 1:100, and incubating overnight at 4° C.; replacing the primary antibody with PBS as a negative control;

8. Discarding the liquid, and washing 3 times with PBS, 5 min each time;

9. After aspirating the liquid, adding the secondary antibody (Alexa Fluor 488 donkey anti-rabbit fluorescent secondary antibody, Invitrogen) at a dilution of 1:200, and incubating at room temperature away from light for 60 min;

10. Discarding the liquid, and washing 3 times with PBS, 5 min each time;

11. Discarding the liquid, DAP (sigma-Aldrich) 0I staining, aspirating the liquid, standing at room temperature for 10 min;

12. Discarding the liquid, and washing 3 times with PBS, 5 min each time;

13. Adding anti-fluorescence quenching sealing agent (sealing with 50% glycerin)

14. Observing and taking pictures with under a fluorescence microscope.

The results were shown in FIG. 3. Gre The results show that the purity of fetal rat cortical neurons of primary culture was more than 90%, and the culture was successful.

Oxygen-Glucose Deprivation (OGD)-Induced Damage to Neurons and Protection of the EPO-Derived Peptide of the Present Invention The fetal rat cortical neurons of primary culture were cultured in a sugar-free DMED culture medium. After being placed in the hypoxic incubator to damage neurons for 3 h, the culture medium were replaced with serum-free culture medium. EPO, the novel EPO-derived peptide (T3) and the culture medium were added to different groups respectively, and the groups were cultured in a 5% $CO_2$ normal oxygen incubator for 4 h. Then the LDH release rate and MTT cell survival rate of each group were measured.

Based on the above results, the primary cortical neurons were administered with 250 μmol/L NMDA. After culturing for 60 min, the results were shown in FIG. 5A and FIG. 5B.

The specific operation process is as follows:

1. Selecting well-grown neurons cultured for 7-14 days, aspirating the old culture medium of neurons, washing 3 times with PBS buffer, and then adding sugar-free DMEM:

2. Placing the culture plates in an anoxic incubator at 37° C., and setting the oxygen concentration therein as 1%.

3. Removing the culture plates after 3 h of hypoxia, aspirating the sugar-free medium, replacing it with the original serum-free maintenance medium, adding EPO (5 μg/ml, 100 μg/ml), the EPO-derived peptide of the present invention (5 μg/ml, 50 μg/ml, 100 μg/ml), and the culture medium respectively, and placing in an 5% $CO_2$ incubator with 95% air at 37° C. for 4 h.

4. After 4 h, measuring the cell survival rate (MTT kit, Beyotime Biotechnology Co., Ltd.) and LDH lactic dehydrogenase release rate (LDH kit, Promega Corporation) of the cells in each group.

Figure 4:
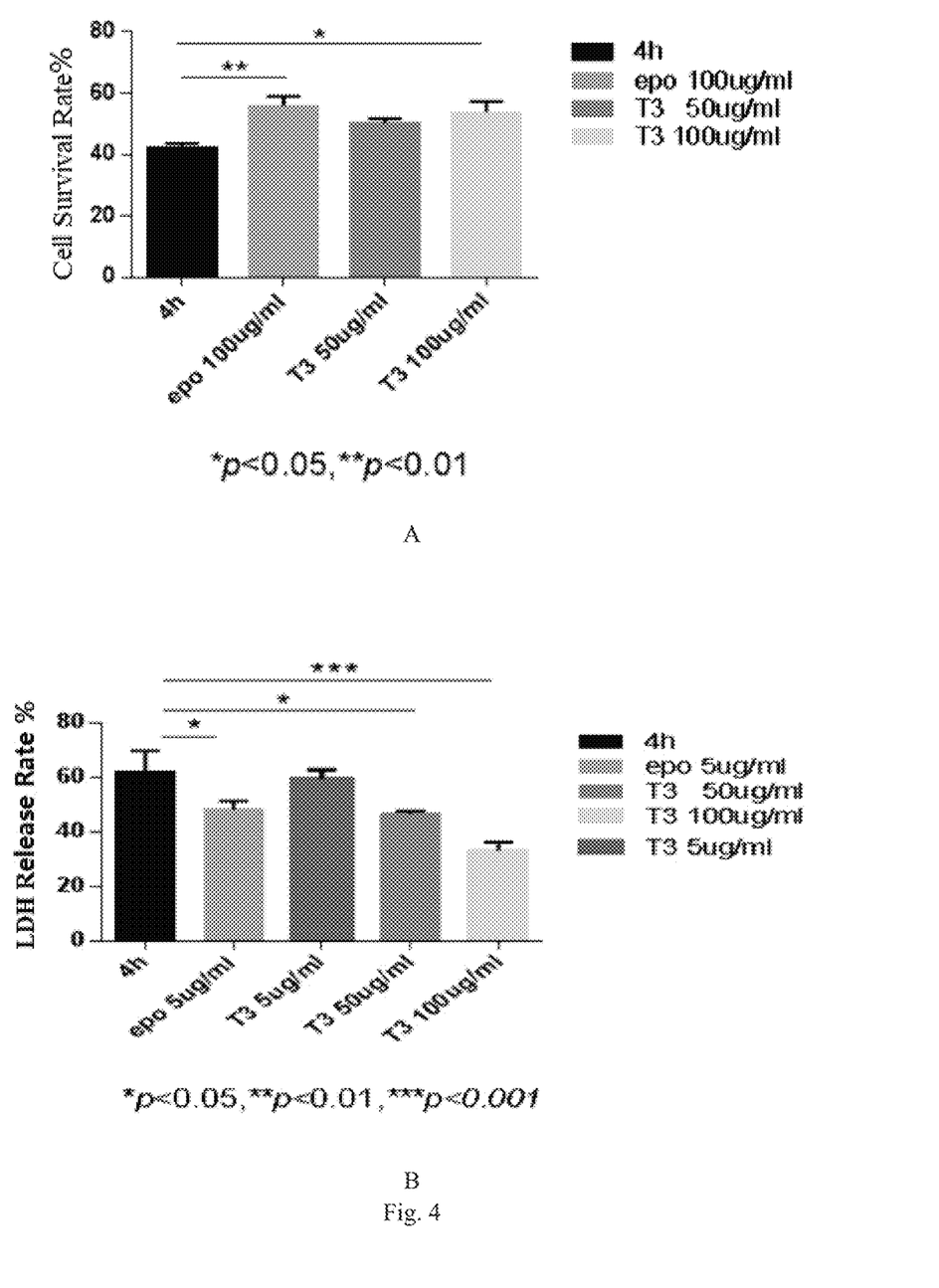
FIG. 4A shows the cell survival rate of the neurons damaged by oxygen-glucose deprivation with different drug interventions; wherein, abscissa: grouping, and ordinate: cell survival rate.
FIG. 4B shows the lactate dehydrogenase release rate of the neurons damaged by oxygen-glucose deprivation with different drug interventions; wherein the abscissa represents grouping, and the ordinate represents lactate dehydrogenase release rate.

The results were shown in FIG. 4A and FIG. 4B. The LDH release rates in the EPO groups and EPO-derived peptide groups (T3) of the present invention were lower than that in the control group, and the cell survival rates thereof were higher than that in the control group, indicating that the EPO-derived peptide of the present invention could alleviate acute nerve damage and reduce neuronal apoptosis.

N-methyl D-aspartate (NMDA)-Induced Damage to Neurons and Protection of the EPO-Derived Peptide of the Present Invention 1. Selecting well-grown neurons cultured for 7-14 days, and adding EPO (5 μg/ml), the EPO-derived peptide of the present invention (100 μg/ml) respectively;

2. Adding NMDA to achieve a final concentration of 250 μmol/L, and culturing in an incubator at 37° C. for 60 min;

3. Discarding the culture medium, and measuring the cell survival rate (MTT kit, Beyotime Biotechnology Co., Ltd.) and LDH lactic dehydrogenase release rate (LDH kit, Promega Corporation) of the cells in each group.

Figure 5:
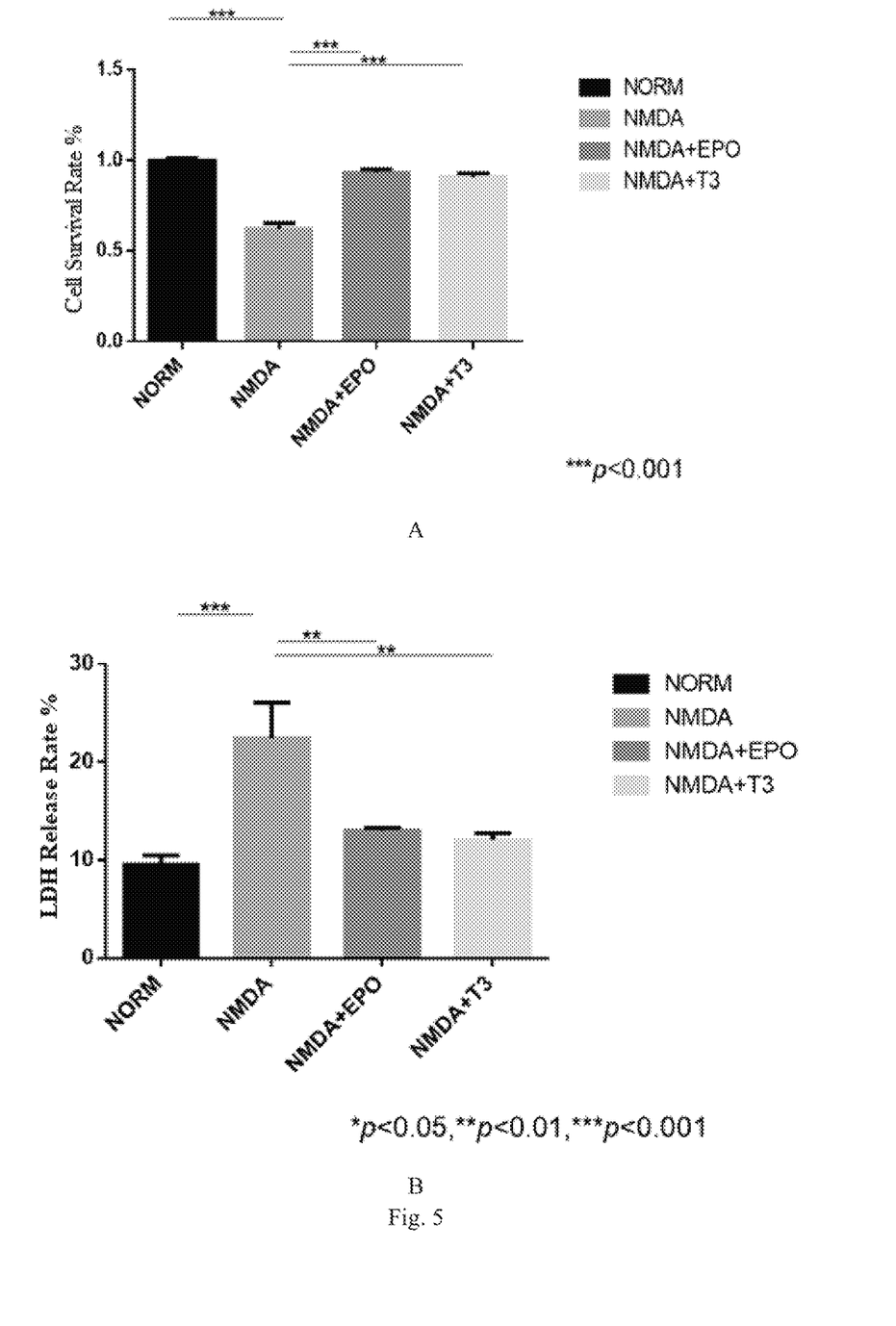
FIG. 5A shows the cell survival rate of the neurons damaged by NMDA with different drug interventions; wherein the abscissa represents grouping, and the ordinate represents cell survival rate.
FIG. 5B shows the lactate dehydrogenase release rate of the neurons damaged by NMDA with different drug interventions: wherein the abscissa represents grouping, and the ordinate represents lactate dehydrogenase release rate.

The results were shown in FIG. 5A and FIG. 5B. The LDH release rates in the EPO group and EPO-derived peptide group (T3) of the present invention were lower than that in the control group, and the cell survival rates thereof were higher than that in the control group, indicating that the EPO-derived peptide of the present invention could alleviate acute nerve damage and reduce neuronal apoptosis.

Embodiment 4: Blood-Brain Barrier Penetration Experiment of the EPO-Derived Peptide of the Present Invention The biotin-labeled novel EPO-derived peptide was injected intraperitoneally. 5-15 μl of mouse cerebrospinal fluid was taken under general anesthesia 1 h after administration. The biotin assay kit was used to detect whether the biotin-labeled novel EPO-derived peptide entered the cerebrospinal fluid across the blood-brain barrier. The results were shown in FIG. 6.

The specific operation process is as follows:

1. Anesthetizing the mouse with 4% chloral hydrate;
2. Wiping the nape of the neck with wet gauze, and cutting off the dorsal set to expose the skin; making a sagittal incision in the skin below the occipital bone, and separating the skin from both sides to expand the visual field;
3. Letting the mouse prone, placing the body at an angle of 135° to the head and fixing the head on the stereotactic instrument; bluntly separating the subcutaneous tissue and muscle along the midline under the stereo microscope; at this angle, the dura mater and spinal cord can be clearly seen in the incision below the occipital bone (The main features are a clear white appearance, a cyclical pulsation of the spinal cord blood vessels and an adjacent cerebrospinal fluid area);
4. Setting the heat value as 300 and the pressure value as 330 in the needle puller, pulling the capillary glass tube into a pointed capillary tube, and trimming the tip of the pointed capillary tube with scissors to make the blunt tip have a diameter of 0.5 mm;
5. Connecting the capillary glass tube to the negative pressure device, and maintaining the negative pressure state of the collection system in advance;
6. Wiping the blood with the cotton swab, and maintaining a clear view around the puncture point;
7. Avoiding the vascular distribution area, facing the cisterna magna, and operating under stereoscopic microscope, slowly puncturing the dura mater with the pointed capillary glass tube; the cerebrospinal fluid can be seen to flow into the glass tube after puncturing: waiting for the cerebrospinal fluid to slowly rise to 5-20 µl; more cerebrospinal fluid can be collected by increasing the negative pressure properly;
8. Slowly removing the glass tube after the cerebrospinal fluid in the tube no longer rose to more volume or is sufficient, transferring the cerebrospinal fluid to the 1.5 ml Eppendorf tube, cryopreserving at −80° C. after centrifugation or detecting immediately;

The cerebrospinal fluid of the mice in the control group, the biotin-labeled EPO-derived peptide of the present invention group, and the epilepsy and biotin-labeled EPO-derived peptide of the present invention group were respectively taken to detect the biotin concentrations by the biotin assay kit.

TABLE 3

Biotin concentrations of cerebrospinal fluid in mice of different administration groups

| | Ctrl group | Ctrl + T3 group | Epilepsy group + T3 group |
|---|---|---|---|
| Concentration of biotin-labeled T3 peptide in cerebrospinal fluid µg/ml | 0.37 ± 0.11 | 1.67 ± 0.30 | 1.97 ± 0.51 |

Figure 6:
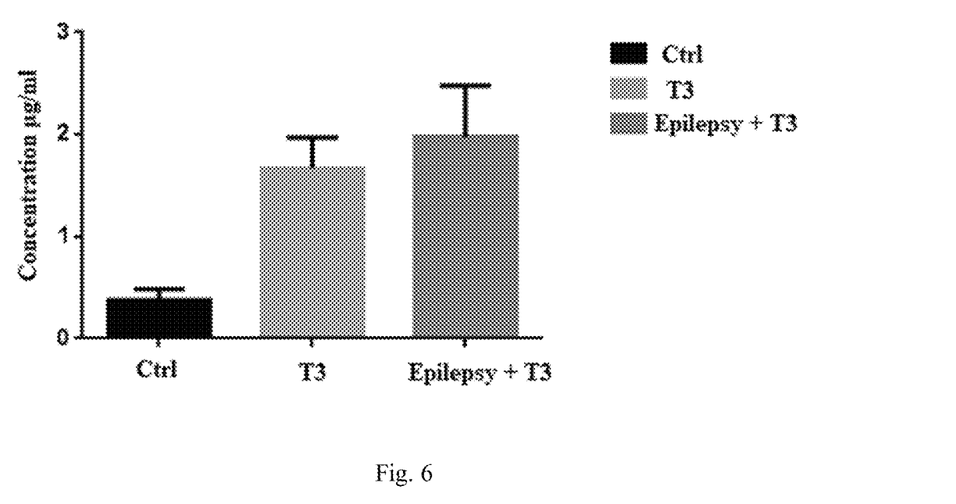
FIG. 6 shows the biotin concentrations of cerebrospinal fluid of mice from different administration groups; wherein the abscissa represents grouping, and the ordinate represents biotin concentration.

The results were shown in FIG. 6. Biotin could be detected in the cerebrospinal fluid of the mice of the EPO-derived peptide of the present invention group, while the control group was almost free of biotin, and the difference was statistically significant. The biotin concentration in the cerebrospinal fluid of the mice in the post-epileptic administration group was higher than that in the single administration group, indicating that the blood-brain barrier was destroyed and the permeability was increased after epilepsy seizure. In summary, the EPO-derived peptide of the present invention could enter the cerebrospinal fluid across the blood-brain barrier to exert its effects.

Embodiment 5: Neuroprotective Effect Experiment of the EPO-Derived Peptide of the Present Invention on a Mouse Model of Transient Middle Cerebral Artery Occlusion ICR mice (male, 25-30 g, 18 mice, purchased from Shanghai Slac Laboratory Animal Co., Ltd.) were divided into control group (ACN+Millq, 0.2 ml/mouse), EPO group (50 µg/kg), novel EPO-derived peptide group (T3, 500 µg/kg), 6 mice/group. Mice in each group were operated with suture-occluded method in mice to establish middle cerebral artery occlusion model, the mice were anesthetized by intraperitoneal injection of ketamine hydrochloride and fixed on the operating table. After 60 min of ischemia, the sutures were removed to reperfuse, and the solvents (ACN+Milliq), EPO, and T3 were administered separately. Neurobehavioral scores were measured on the third day after surgery, and then the mice were sacrificed to reperfuse and the brains were harvested to make sections stained with cresyl violet. The results were shown in FIG. 7A, FIG. 7B and FIG. 7C.

1. Disinfecting the neck, making an incision at the center of the neck, exposing the left common carotid artery with a microsurgical forceps under a stereo microscope, separating the internal carotid artery, external carotid artery and pterygopalatine artery, ligating the common carotid artery and internal carotid artery; making two knots on the external carotid artery with two filaments, wherein one at the distal part of the external carotid artery is a dead knot, and one at the proximal part of the external carotid artery is a slipknot;
2. Making a small incision on the external carotid artery with venus scissors, having about half the size of the blood vessel;
3. Cutting the external carotid artery, and carefully reversely inserting the suture from the external carotid artery into the bifurcation of the external carotid artery and internal carotid artery, then loosening the knot on the internal carotid artery, inserting the suture into the internal carotid artery until it encounters a slight resistance, that is, the origin of the middle cerebral artery, and putting the mouse back into the cage.
4. Anesthetizing and fixing again after 60 min of cerebral ischemia, and re-exposing the common carotid artery, internal carotid artery and suture parts under a stereo microscope;
5. Loosening the filament ligated to the proximal part of the external carotid artery for fixing the suture with the microsurgical forceps, slowly withdrawing the suture, and ligating the stump of the external carotid artery, loosening the filament ligated to the common carotid artery to achieve reperfusion;
6. Suturing the incision of the neck, disinfecting the area, and putting the mouse back in the cage for observation.

TABLE 4

Neurobehavioral scores of mice in different administration groups

| | Ctrl group | Ctrl + T3 group | Epilepsy group + T3 group |
|---|---|---|---|
| Neurobehavioral scores | 8.0 ± 1.0 | 6.3 ± 0.7 | 5.7 ± 0.3 |

TABLE 5

Cerebral infarction volumes of transient middle cerebral artery occlusion in mice of different administration groups

|  | Ctrl group | ctrl + T3 group | Epilepsy group + T3 group |
|---|---|---|---|
| Cerebral infarction volumes (mm³) | 49.65 ± 10.29 | 40.54 ± 5.78 | 37.72 ± 9.20 |

Figure 7A:
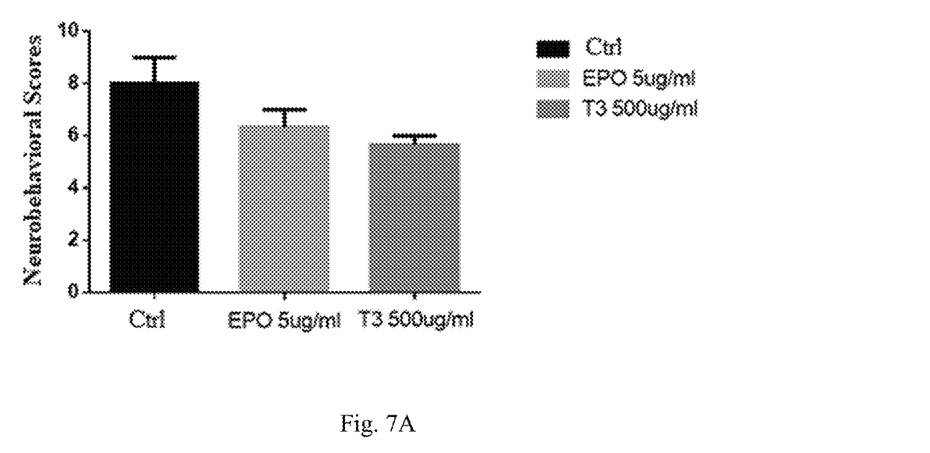
FIG. 7A shows the neurobehavioral scores of mice from different administration groups, wherein the abscissa represents grouping, and the ordinate represents neurobehavioral scores.
Figure 7B:
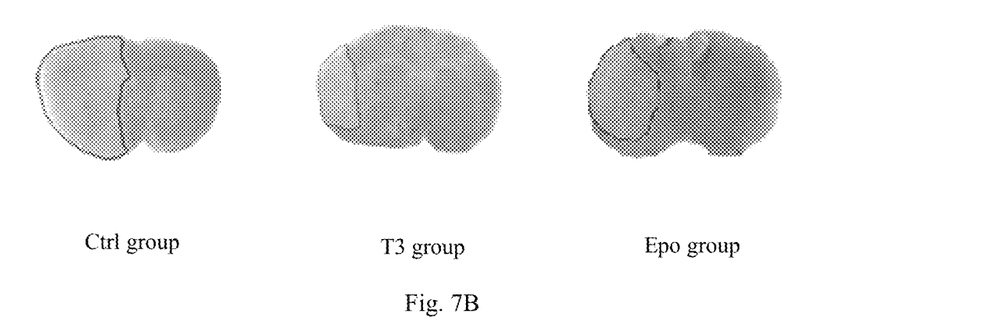
FIG. 7B shows images of transient middle cerebral artery occlusion of mice from different administration groups.
Figure 7C:
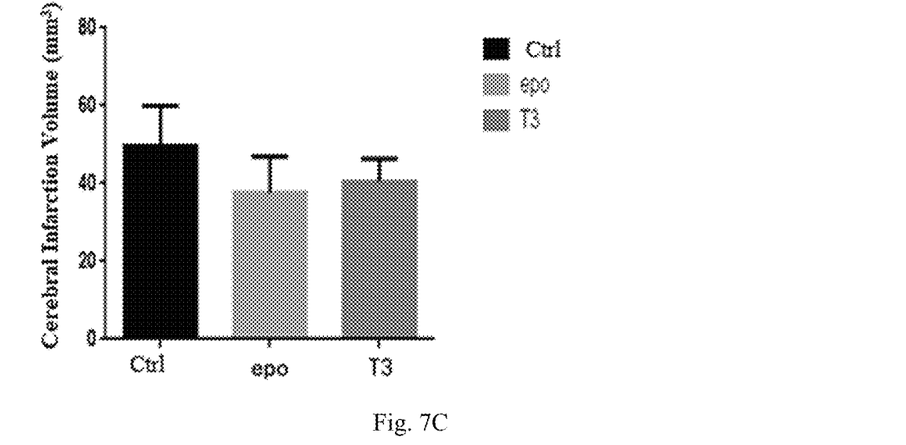
FIG. 7C shows the cerebral infarction volumes of transient middle cerebral artery occlusion of mice from different administration groups, wherein the abscissa represents grouping, and the ordinate represents cerebral infarction volume.

The results were shown in FIG. 7A. FIG. 7B and FIG. 7C. The neurobehavioral scores and cerebral infarction volume of the EPO group and the EPO-derived peptide of the present invention group were lower than those of the control group, indicating that EPO and the EPO-derived peptide of the present invention could improve cerebral ischemia in vivo and have neuroprotective effects.

Embodiment 6: Neuroprotective Effect Experiment of the EPO-Derived Peptide of the Present Invention on an Animal Model of Epilepsy C57/BL6 mice (male, 20-25 g, 24 mice, purchased from Shanghai JieSiJie Laboratory Animal Co., Ltd) were divided into physiological saline group (Saline, 0.2 ml/mouse), solvent group (ACN+Milliq, 0.2 ml/mouse), EPO group (50 µg/kg), novel EPO-derived peptide group (T3, 500 µg/kg), 6 mice each group. The drugs were administered 1 day, 4 h, and 2 h before pilocarpine-induced epilepsy, and the seizure latency and severity of seizures were recorded. The results were shown in FIG. 8.
1. Intraperitoneally administering the mice 1 day, 4 h, 2 h prior to the injection of pilocarpine;
2. Intraperitoneally injecting scopolamine (1 mg/kg) 30 min in advance to reduce the peripheral cholinergic response induced by pilocarpine;
3. Intraperitoneally injecting pilocarpine (350 mg/kg), recording the time of administration, time of onset, severity of seizure;
4. After the seizures of more than grade IV, spontaneous activity and epilepsy continuing status occurred, indicating that the model was established successfully; 30 min after successfully establishing the model, administering diazepam (10 mg/kg) to stop the seizures.

Behavioral grading of epilepsy continuing status using the Racine scale:
 Grade I: staring, mouth and facial movements;
 Grade II: nodding, single jerks;
 Grade III: unilateral/bilateral forelimb clonus
 Grade IV: rearing;
 Grade V: loss of posture, jumping repeatedly, falling, tonic clonic seizure.

TABLE 6

Seizure latencies of mice after pilocarpine-induced seizures with different drug interventions

|  | epo | T3 | Saline | ACN + miliq |
|---|---|---|---|---|
| seizure latency(min) | 41.16 ± 3.52 | 40.58 ± 3.67 | 32.50 ± 1.80 | 27.20 ± 2.48 |

Figure 8:
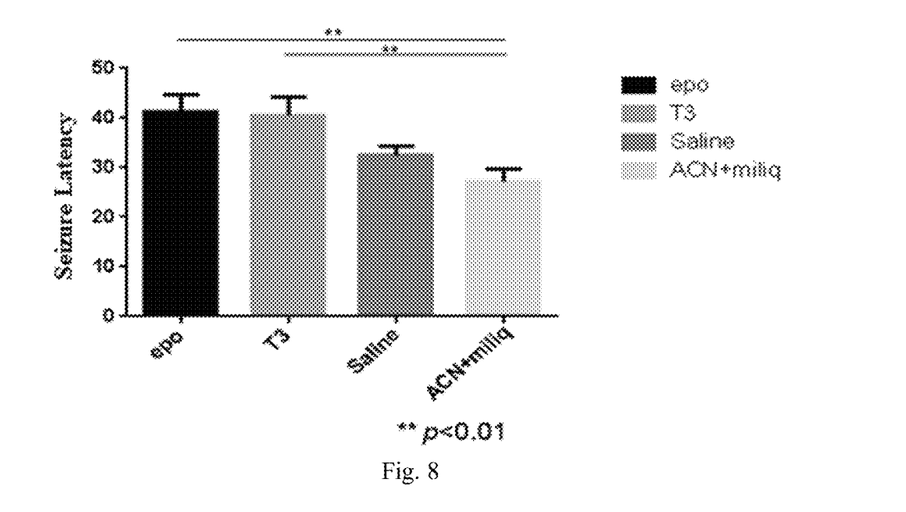
FIG. 8 shows the seizure latencies of mice after pilocarpine-induced seizures with different drug interventions, wherein the abscissa represents grouping, and the ordinate represents seizure latency.

The results were shown in FIG. 8. The seizure latency of the EPO group and the EPO-derived peptide of the present invention group were longer than those of the physiological saline group and the solvent group, and the difference was statistically significant, indicating that the EPO and the EPO-derived peptide of the present invention had neuroprotective effects in vivo.

Embodiment 7

When the EPO-derived peptide of the present invention is prepared into a medicament, an effective amount of the polypeptide, at least one pharmaceutically acceptable carrier, and diluent or excipient can be combined. In the preparation of these compositions, the active ingredient is usually mixed with excipients, or diluted with excipients, or encapsulated in a carrier which may be in the form of a capsule or pouch. When the excipient acts as a diluent, it can be a solid, semi-solid or liquid material as a medium for excipient, carrier or active ingredient. Therefore, the medicament can be a tablet, a pill, a powder, a solution, a syrup, a sterile injectable solution, etc. Examples of the suitable excipients include: lactose, glucose, sucrose, sorbitol, mannitol, starch, microcrystalline cellulose, polyvinylpyrrolidone, cellulose, water, etc. The preparation also includes a wetting agent, an emulsifier, a preservative (such as methyl hydroxybenzoate and propyl hydroxybenzoate), a sweetener, etc.

In summary, the novel EPO-derived peptide of the present invention can protect neuronal cells and reduce apoptosis in acute injury; long-term administration to mice has no significant side effects of erythropoiesis; it can penetrate the blood-brain barrier, reduce the cerebral infarction volume and improve cerebral ischemia with administration after ischemic damage in vivo, and prolong seizure latency with pre-administration, thus confirming that it can be used to prepare medicaments for treating nerve damage. The hematopoietic experiment in vivo was carried out on the EPO-derived peptide of the present invention, confirming that it has no erythropoiesis effects. Furthermore, the inventors confirmed that the novel EPO-derived peptide has neuroprotective effects by anti-apoptosis experiments of cortical neurons in vitro. The biotin-labeled polypeptide in the cerebrospinal fluid was detected after administration in animal model, confirming that the novel EPO-derived peptide can penetrate the blood-brain barrier to exert protective effects.

What is claimed is:

1. A nucleic acid molecule, comprising a nucleotide sequence encoding an erythropoietin-derived peptide comprising an amino acid sequence as shown in SEQ ID NO: 1.

2. An expression vector, comprising the nucleic acid molecule of claim 1.

3. A host cell, comprising the nucleic acid molecule of claim 1 or an expression vector comprising the nucleic acid molecule of claim 1.

4. A virus, comprising the nucleic acid molecule of claim 1 or an expression vector comprising the nucleic acid molecule of claim 1.

5. A kit, comprising any one of the following:
a) the nucleic acid molecule of claim 1;
b) an expression vector comprising the nucleic acid molecule of a);
c) a host cell comprising the nucleic acid molecule of a) or the expression vector of b);
d) a virus comprising the nucleic acid molecule of a) or the expression vector of b).

6. An erythropoietin-derived peptide, comprising an amino acid sequence as shown in SEQ ID NO: 1, further comprising EPO and EPOR binding sites and an amino acid sequence of EPO protein helix structure, wherein the erythropoietin-derived peptide has no erythropoiesis effect, but has neuroprotective effects.

7. The erythropoietin-derived peptide of claim 6, wherein one or more positions selected from the group consisting of glutamine at position 86, tryptophan at position 88, glutamate at position 89, proline at position 90, and lysine at position 97 in the amino acid sequence of the EPO protein helix structure are deleted.

8. The erythropoietin-derived peptide of claim 6, wherein arginine at position 103 in the amino acid sequence of the EPO protein helix structure is replaced with alanine.

9. The erythropoietin-derived peptide of claim 6, wherein the erythropoietin-derived peptide has a following structural formula:

10. A medicament, comprising the erythropoietin-derived peptide of claim 6, wherein the erythropoietin-derived peptide is combined with at least one of a pharmaceutically acceptable carrier and a diluent or excipient.

11. A composition, comprising the erythropoietin-derived peptide of claim 6, wherein the erythropoietin-derived peptide is combined with at least one of a carrier and a diluent or excipient.

12. A kit, comprising any one of the following:
a) the erythropoietin-derived peptide of claim 6 and at least one of a carrier and a diluent or excipient;
b) a composition comprising the erythropoietin-derived peptide of claim 6.

13. A use of the erythropoietin-derived peptide of claim 6 for treating nerve cell damage, wherein the erythropoietin-derived peptide is administered to a subject having nerve cell damage as a tablet, a pill, a powder, a solution, a syrup, or a sterile injectable solution.

14. A use of the erythropoietin-derived peptide of claim 6 for treating hypoxic brain damage, wherein the erythropoietin-derived peptide is administered to a subject having hypoxic brain damage as a tablet, a pill, a powder, a solution, a syrup, or a sterile injectable solution.

15. An erythropoietin-derived peptide having no erythropoiesis effect but having neuroprotective effects, comprising a polypeptide having an amino acid sequence as shown in SEQ ID NO: 1.

16. A preparation method of the erythropoietin-derived peptide of claim 15, comprising the following steps:
(1) adopting a solid phase synthesis method, immersing a starting resin in N,N-dimethylformamide, wherein leucine is attached to the starting resin, then immersing the starting resin in a decapping solution to remove any fluorenylmethoxycarbonyl of the starting resin, and washing the starting resin with dimethylformamide to obtain a first non-fluorenylmethoxycarbonyl resin;
(2) adding a next amino acid, condensing agent and base to the non-fluorenylmethoxycarbonyl resin, and then washing the non-fluorenylmethoxycarbonyl resin with dimethylformamide after reacting of the next amino acid, the condensing agent, the base, and the non-fluorenylmethoxycarbonyl resin to obtain a second resin;
(3) removing fluorenylmethoxycarbonyl of the second resin with the decapping solution, and then washing the second resin with dimethylformamide to obtain a third non-fluorenylmethoxycarbonyl resin;
(4) repeating steps (2) and (3) to sequentially link amino acids.

17. The preparation method of the erythropoietin-derived peptide of claim 16, wherein the condensing agent in step (2) is O-benzotriazole-N,N,N',N'-tetramethyluronium tetrafluoroborate.

18. The preparation method of the erythropoietin-derived peptide of claim 16, wherein the base in step (2) is morpholine.

19. The preparation method of the erythropoietin-derived peptide of claim 16, wherein the decapping solution in step (3) is a mixture of hexahydropyridine and N, N-dimethylformamide.

\* \* \* \* \*

SEQUENCE LISTING

```
<160> NUMBER OF SEQ ID NOS: 1

<210> SEQ ID NO 1
<211> LENGTH: 37
<212> TYPE: PRT
<213> ORGANISM: Artificial Sequence
<220> FEATURE:
<223> OTHER INFORMATION: A synthetized amino acid sequence of an
      erythropoietin-derived peptide

<400> SEQUENCE: 1

Ser Glu Ala Val Leu Arg Gly Gln Ala Leu Leu Val Asn Ser Ser Pro
```

```
                                           -continued
1              5                  10                 15
Leu Gln Leu His Val Asp Ala Val Ser Gly Leu Ala Ser Leu Thr Thr
                20                  25                 30
Leu Leu Arg Ala Leu
            35
```